United States Patent
Arnold et al.

(10) Patent No.: US 8,318,457 B2
(45) Date of Patent: Nov. 27, 2012

(54) FSH PRODUCING CELL CLONE

(75) Inventors: Stefan Arnold, Schwetzingen (DE); Nanni Jelinek, Mannheim (DE)

(73) Assignee: BioGeneriX AG, Mannheim (DE)

( * ) Notice: Subject to any disclaimer, the term of this patent is extended or adjusted under 35 U.S.C. 154(b) by 197 days.

(21) Appl. No.: 12/666,257

(22) PCT Filed: Jun. 27, 2008

(86) PCT No.: PCT/EP2008/058274
§ 371 (c)(1),
(2), (4) Date: Jun. 2, 2010

(87) PCT Pub. No.: WO2009/000913
PCT Pub. Date: Dec. 31, 2008

(65) Prior Publication Data
US 2012/0034655 A1 Feb. 9, 2012

(30) Foreign Application Priority Data
Jun. 28, 2007 (EP) .................................. 07111257

(51) Int. Cl.
A61K 38/24 (2006.01)
C07K 1/00 (2006.01)
C12N 5/00 (2006.01)
C12N 5/071 (2010.01)
C12N 15/09 (2006.01)
C12N 15/16 (2006.01)
C12P 21/00 (2006.01)

(52) U.S. Cl. ..................... 435/69.4; 435/69.7; 435/70.1; 435/325; 435/358; 435/365.1; 530/350; 530/399; 514/9.9

(58) Field of Classification Search .................. None
See application file for complete search history.

(56) References Cited

U.S. PATENT DOCUMENTS

| 7,901,905 | B2 * | 3/2011 | Frazer ........................... 435/69.1 |
| 2002/0127652 | A1 | 9/2002 | Schambye |
| 2007/0281883 | A1 | 12/2007 | Rosenfeld |

FOREIGN PATENT DOCUMENTS

| EP | 0404546 | | 12/1990 |
| WO | WO 96/25496 | | 8/1997 |
| WO | WO/01/58493 | * | 8/2001 |
| WO | WO 01/58493 | | 8/2001 |
| WO | WO2005/030969 | * | 9/2004 |
| WO | WO 2005/030969 | | 4/2005 |
| WO | WO 2007/003640 | | 1/2007 |

OTHER PUBLICATIONS

Lim et al., High-level expression of a codon optimized recombinant dust mite allergen, Blo t 5, in Chinese hamster ovary cells, Biochem. Biophys. Res. Comm. 316, 991-996, 2004.*
Wang, et al. 2006. "Codon usage of Chinese hamster ovary cells." Chinese J Exp Clin Virol. 20(3):266-269.
Gustafsson, et al. 2004. "Codon bias and heterologous protein expression." Trends in Biotechnology 22(7):346-352.
Keene, et al. 1989, "Expression of biologically active human follitropin in Chinese hamster ovary cells." The Journal of Biological Chemistry 264(9):4769-4775.
P01215, "Glycoprotein homones alpha chain precursor—Homo sapiens (Human)," Version 136, Rev. Jul. 2012, UniProt Database [online] [retrieved on Aug. 9, 2012].
P01225, "Follitropin subunit beta precursor—Homo sapiens (Human)," Version 137, Rev. Jul. 2012, UniProt Database [online] [retrieved on Aug. 9, 2012].
Rathnam, P and Saxena, B, "Primary Amino Acid Sequence of Follicle-stimulating Hormone from Human Pituitary Glands," J Biol Chem, Sep. 1975, 250(17): 6735-6746.
Saxena, B and Rathnam, P, "Amino Acid Sequence of the β Subunit of Follicle-stimulating Hormone from Human Pituitary Glands," J Biol Chem, Feb. 1976, 251(4): 993-1005.

* cited by examiner

*Primary Examiner* — Elly-Gerald Stoica
(74) *Attorney, Agent, or Firm* — Davis Wright Tremaine LLP

(57) ABSTRACT

The present invention relates to nucleic acid molecules comprising a nucleic acid sequence coding for the α- and the β-chain of the human follicle stimulating hormone (FSH), respectively, which has been modified with respect to the codon usage in CHO cells. The present invention further relates to a recombinant nucleic acid molecule comprising such nucleic acid sequences and host cells containing such recombinant nucleic acid molecules, as well as their use in the production of recombinant human FSH. Finally, the present invention also relates to a method for producing host cells expressing human follicle stimulating hormone by transfecting cells in suspension culture under serum-free conditions with the recombinant nucleic acid molecule of the present invention.

22 Claims, 4 Drawing Sheets

```
pXM17ss    3398   cttaattaagccgccagcatggactactacaggaagtacgccgccatcttcctggtgacc
3457
                  ||||||||||||||||||||||||| |||||||| || || || || ||||| ||||| ||
wt αFSH    65     cttaattaagccgccagcatggattactacagaaaatatgcagctatctttctggtcaca
124 pXM17ss    3458   ctgagcgtgttcctgcacgtgctgcacagcgccccagacgtgcaggactgccccgagtgc
3517
                  ||    ||||| ||||| || || ||    ||| || || |||||||| ||||| || |||
wt αFSH    125    ttgtcggtgtttctgcatgttctccattccgctcctgatgtgcaggattgcccagaatgc
184 pXM17ss    3518   accctgcaggagaacccattcttcagccagcccggagcccccatcctgcagtgcatgggc
3577
                  || || ||||| |||||||||||| |||||| || ||||| || || ||||||||||||
wt αFSH    185    acgctacaggaaaacccattcttctcccagccgggtgccccaatacttcagtgcatgggc
244 pXM17ss    3578   tgctgcttcagcagggcctaccccaccccctgaggagcaagaagaccatgctggtgcag
3637
                  ||||||||    || || || ||||| || || |||    |||||||| ||| |||| ||
wt αFSH    245    tgctgcttctctagagcatatcccactccactaaggtccaagaagacgatgttggtccaa
304 pXM17ss    3638   aagaacgtgaccagcgagagcacctgctgcgtggccaagagctacaacagggtgaccgtg
3697
                  |||||||| |||   |||   ||| ||||| || || ||    || |||||||| || ||
wt αFSH    305    aagaacgtcacctcagagtccacttgctgtgtagctaaatcatataacagggtcacagta
364 pXM17ss    3698   atgggcggcttcaaggtggagaaccacaccgcctgccactgcagcacctgctactaccac
3757
                  ||||| || ||||| |||||||||||||| || |||||||||| || || || || |||
wt αFSH    365    atgggggtttcaaagtggagaaccacacggcgtgccactgcagtacttgttattatcac
424 pXM17ss    3758   aagagctaatga        3769
                  ||    |||
wt αFSH    425    aaatcttaa           433
```

Fig. 1a

```
Query: 1    aggatccccgggctacctccccgcggggaggcgcgccccttaattaagccgccaccatga 60
            |||||||||||| |||||||||||||||||||||||||||||||||||||||||||||||
Sbjct: 2    aggatccccggg-tacctccccgcggggaggcgcgccccttaattaagccgccaccatga 60

Query: 61   agacactccagttttcttccttttctgttgctggaaagcaatctgctgcaatagctgtg 120
            ||||  ||||| ||||||||||| ||| |||||||||  || |||||||||||  ||||| |
Sbjct: 61   agaccctgcagttcttcttcctgttctgctgctggaaggccatctgctgcaacagctgcg 120

Query: 121  agctgaccaacatcaccattgcaatagagaaagaagaatgtcgtttctgcataagcatca 180
            |||||||||||||||||||| || || |||||  || ||  |  | ||||||| |||||||
Sbjct: 121  agctgaccaacatcaccatcgccatcgagaaggaggagtgcaggttctgcatcagcatca 180

Query: 181  acaccacttggtgtgctggctactgctacaccagggatctggtgtataaggacccagcca 240
            |||||||  ||||| ||  ||  |||||||||||||| ||||||| ||||||||| ||||
Sbjct: 181  acaccacctggtgcgccggatactgctacaccagggacctggtgtacaaggaccccgcca 240

Query: 241  ggcccaaaatccagaaaacatgtaccttcaaggaactggtatatgaaacagtgagagtgc 300
            |||||||  ||||||| |  ||  ||||||||||| ||||||| || || || ||| ||||
Sbjct: 241  ggcccaagatccagaagacctgcaccttcaaggagctggtgtacgagaccgtgagggtgc 300

Query: 301  ccggctgtgctcaccatgcagattccttgtatacatacccagtggccacccagtgtcact 360
            |||||||  || |||||  || ||    |||| || ||||| |||||||||||||  ||||
Sbjct: 301  ccggctgcgcccaccacgccgacagcctgtacacctaccccgtggccacccagtgccact 360

Query: 361  gtggcaagtgtgacagcgacagcactgattgtactgtgcgaggcctggggcccagctact 420
            | |||||||| |||||||||||||| |  || || |||  ||||||||||||||||||||
Sbjct: 361  gcggcaagtgcgacagcgacagcaccgactgcaccgtgaggggcctgggcccagctact 420

Query: 421  gctcctttggtgaaatgaaagaataaacatgccatggcatgcgagctcgaattc 474
            ||  ||| || || ||||| ||  |||  |   ||||||||||||||||||||||
Sbjct: 421  gcagcttcggcgagatgaaggagtaatga--ccatggcatgcgagctcgaattc 472
```

Fig. 1b

SEQUENCE LISTING

```
<160> NUMBER OF SEQ ID NOS: 13

<210> SEQ ID NO 1
<211> LENGTH: 471
<212> TYPE: DNA
<213> ORGANISM: Artificial
<220> FEATURE:
<223> OTHER INFORMATION: Modified beta chain
```

<400> SEQUENCE: 1

```
aggatcccccg ggtacctccc cgcggggagg cgcgccccctt aattaagccg ccaccatgaa      60
gaccctgcag ttcttcttcc tgttctgctg ctggaaggcc atctgctgca acagctgcga     120
gctgaccaac atcaccatcg ccatcgagaa ggaggagtgc aggttctgca tcagcatcaa     180
caccaccctgg tgcgccggat actgctacac cagggacctg gtgtacaagg accccgccag    240
gcccaagatc cagaagacct gcaccttcaa ggagctggtg tacgagaccg tgagggtgcc     300
cggctgcgcc caccacgccg acagcctgta cacctacccc gtggccaccc agtgccactg     360
cggcaagtgc gacagcgaca gcaccgactg caccgtgagg ggcctgggcc ccagctactg     420
cagcttcggc gagatgaagg agtaatgacc atggcatgcg agctcgaatt c              471
```

<210> SEQ ID NO 2
<211> LENGTH: 372
<212> TYPE: DNA
<213> ORGANISM: Artificial
<220> FEATURE:
<223> OTHER INFORMATION: Modified alpha chain

<400> SEQUENCE: 2

```
cttaattaag ccgccagcat ggactactac aggaagtacg ccgccatctt cctggtgacc       60
ctgagcgtgt tcctgcacgt gctgcacagc gccccagacg tgcaggactg ccccgagtgc     120
accctgcagg agaacccatt cttcagccag cccggagccc ccatcctgca gtgcatgggc     180
tgctgcttca gcagggccta ccccacccccc tgaggagca agaagaccat gctggtgcag    240
aagaacgtga ccagcgagag cacctgctgc gtggccaaga gctacaacag ggtgaccgtg     300
atgggcgggct tcaaggtgga gaaccacacc gcctgccact gcagcaccctg ctactaccac    360
aagagctaat ga                                                         372
```

<210> SEQ ID NO 3
<211> LENGTH: 369
<212> TYPE: DNA
<213> ORGANISM: Homo sapiens

<400> SEQUENCE: 3

```
cttaattaag ccgccagcat ggattactac agaaaatatg cagctatctt tctggtcaca       60
ttgtcggtgt ttctgcatgt tctccattcc gctcctgatg tgcaggattg cccagaatgc     120
acgctacagg aaaacccatt cttctcccag ccgggtgccc caatacttca gtgcatgggc     180
tgctgcttct ctagagcata tcccactcca ctaaggtcca agaagacgat gttggtccaa     240
aagaacgtca cctcagagtc cacttgctgt gtagctaaat catataacag ggtcacagta     300
atgggggggtt tcaaagtgga gaaccacacg gcgtgccact gcagtacttg ttattatcac     360
aaatcttaa                                                             369
```

<210> SEQ ID NO 4
<211> LENGTH: 474
<212> TYPE: DNA
<213> ORGANISM: Homo sapiens

<400> SEQUENCE: 4

```
aggatcccccg ggctacctcc ccgcggggag gcgcgcccct taattaagcc gccaccatga      60
agacactcca gttttttcttc cttttctgtt gctggaaagc aatctgctgc aatagctgtg     120
agctgaccaa catcaccatt gcaatagaga agaagaatg tcgttctgc ataagcatca       180
acaccacttg gtgtgctggc tactgctaca ccagggatct ggtgtataag gacccagcca     240
```

```
ggcccaaaat ccagaaaaca tgtaccttca aggaactggt atatgaaaca gtgagagtgc      300
ccggctgtgc tcaccatgca gattccttgt atacataccc agtggccacc cagtgtcact      360
gtggcaagtg tgacagcgac agcactgatt gtactgtgcg aggcctgggg cccagctact      420
gctcctttgg tgaaatgaaa gaataaacat gccatggcat gcgagctcga attc            474
```

```
<210> SEQ ID NO 5
<211> LENGTH: 116
<212> TYPE: PRT
<213> ORGANISM: Homo sapiens

<400> SEQUENCE: 5

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```

```
<210> SEQ ID NO 6
<211> LENGTH: 129
<212> TYPE: PRT
<213> ORGANISM: Homo sapiens

<400> SEQUENCE: 6

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu
```

```
<210> SEQ ID NO 7
<211> LENGTH: 8983
<212> TYPE: DNA
<213> ORGANISM: Artificial
```

<220> FEATURE:
<223> OTHER INFORMATION: Plasmid

<400> SEQUENCE: 7

```
ggaataagaa agcggccgct cactcattag gcaccccagg ctttacactt tatgcttccg      60
gctcgtatgt tgtgtggaat tgtgagcgga taacaatttc acacaggaaa cagctatgac    120
atgattacga attcgagctc ggtacccggg gatccagaca tgataagata cattgatgag    180
tttggacaaa ccacaactag aatgcagtga aaaaaatgct ttatttgtga aatttgtgat    240
gctattgctt tatttgtaac cattataagc tgcaataaac aagttaacaa caacaattgc    300
attcatttta tgtttcaggt tcaggggag gtgtgggagg ttttttaaag caagtaaaac    360
ctctacaaat gtggtatggc tgattatgat ctctagtcaa ggcactatac atcaaatatt    420
ccttattaac ccctttacaa attaaaaagc taaaggtaca caattttga gcatagttat    480
taatagcaga cactctatgc ctgtgtggag taagaaaaaa cagtatgtta tgattataac    540
tgttatgcct acttataaag gttacagaat attttccat aattttcttg tatagcagtg    600
cagctttttc ctttgtggtg taaatagcaa agcaagcaag agttctatta ctaaacacag    660
catgactcaa aaaacttagc aattctgaag gaaagtcctt ggggtcttct acctttctct    720
tcttttttgg aggagtagaa tgttgagagt cagcagtagc ctcatcatca ctagatggca    780
tttcttctga gcaaacagg ttttcctcat taaaggcatt ccaccactgc tcccattcat    840
cagttccata ggttggaatc taaaatacac aaacaattag aatcagtagt ttaacacatt    900
atacacttaa aaattttata tttaccttag agctttaaat ctctgtaggt agtttgtcca    960
attatgtcac accacagaag taaggttcct tcacaaagat cccactacag aagcaatcta   1020
cagtctctat tgcagtttgt aaccccctcc ccctccccc tttaatactg aatgagatcg   1080
aatgttaggt ccatgcagtt cttggtcaat gttaacgaaa gtccaacgtt ccgttcgcgc   1140
ggggacagcc cgtccgcaaa gcggggcagc ccgcaggcgg cccctcgagg tcgacggtat   1200
cgataagctt ggtaccgagc tcggatccac tagtaacggc cgccagtgtg ctggaattcg   1260
gcttgagctc aggcgtcttc ccagcatggc tctgtccctg agtttaaagc tgctctctga   1320
atgcttcctg ctctgggccc tcaagttggc cctgtgacat ccttagatct cagagttgct   1380
ctctggacag ttcctctggc ccctgagatg tcattgctgg cactggagtg tccatggtca   1440
ttactcttc atctcgccga agctgcagta gctggggccc aggcccctca cggtgcagtc   1500
ggtgctgtcg ctgtcgcact tgccgcagtg gcactgggtg gccacggggt aggtgtacag   1560
gctgtcggcg tggtgggcgc agccgggcac cctcacggtc tcgtacacca gctccttgaa   1620
ggtgcaggtc ttctggatct tgggcctggc ggggtccttg tacaccaggt ccctggtgta   1680
gcagtatccg gcgcaccagg tggtgttgat gctgatgcag aacctgcact cctccttctc   1740
gatggcgatg tgatgttgg tcagctcgca gctgttgcag cagatggcct tccagcagca   1800
gaacaggaag aagaactgca gggtcttcat ggtggcggct taattaagtt cgagactgtt   1860
gtgtcagaag aatcaagctt tttgcaaaag cctaggcctc caaaaaagcc tcctcactac   1920
ttctggaata gctcagaggc cgaggcggcc tcggcctctg cataaataaa aaaaattagt   1980
cagccatggg gcggagaatg ggcggaactg ggcggagtta ggggcgggat ggcggagtt   2040
aggggcggga ctatggttgc tgactaattg agatgcatgc tttgcatact ctgcctgct   2100
ggggagcctg gggactttcc acacctggtt gctgactaat tgagatgcat gctttgtata   2160
cttctgcctg ctggggagcc tggggacttt ccacacccta actgacacac attccacagc   2220
tggttctttc cgcctcagaa ggtacctaac caagttcctc tttcagaggt tatttcaggc   2280
```

```
catggtgctg cgcagatcgc ggccgctaaa ctaaggcgcg ccttttgctc acatggctcg   2340
acagatcttc aatattggcc attagccata ttattcattg gttatatagc ataaatcaat   2400
attggctatt ggccattgca tacgttgtat ctatatcata atatgtacat ttatattggc   2460
tcatgtccaa tatgaccgcc atgttggcat tgattattga ctagttatta atagtaatca   2520 attacgggt cattagttca tagcccatat atggagttcc gcgttacata acttacggta   2580
aatggcccgc ctggctgacc gcccaacgac ccccgcccat tgacgtcaat aatgacgtat   2640
gttcccatag taacgccaat agggactttc cattgacgtc aatgggtgga gtatttacgg   2700
taaactgccc acttggcagt acatcaagtg tatcatatgc caagtccgcc cctattgac   2760 gtcaatgacg gtaaatggcc cgcctggcat tatgcccagt acatgacctt acgggacttt   2820
cctacttggc agtacatcta cgtattagtc atcgctatta ccatggtgat gcggttttgg   2880
cagtacacca atgggcgtgg atagcggttt gactcacggg gatttccaag tctccacccc   2940
attgacgtca atgggagttt gttttggcac caaaatcaac gggactttcc aaaatgtcgt   3000
aacaactgcg atcgcccgcc ccgttgacgc aaatgggcgg taggcgtgta cggtgggagg   3060
tctatataag cagagctcgt ttagtgaacc gtcagatcac tagaagcttt attgcggtag   3120
tttatcacag ttaaattgct aacgcagtca gtgcttctga cacaacagtc tcgaacttaa   3180
gctgcagtga ctctcttaag gtagccttgc agaagttggt cgtgaggcac tgggcaggta   3240
agtatcaagg ttacaagaca ggtttaagga gaccaataga aactgggctt gtcgagacag   3300
agaagactct tgcgtttctg ataggcacct attggtctta ctgacatcca ctttgccttt   3360
ctctccacag gtgtccactc ccagttcaat tacagctctt aattaagccg ccagcatgga   3420
ctactacagg aagtacgccg ccatcttcct ggtgaccctg agcgtgttcc tgcacgtgct   3480
gcacagcgcc ccagacgtgc aggactgccc cgagtgcacc ctgcaggaga acccattctt   3540
cagccagccc ggagccccca tcctgcagtg catgggctgc tgcttcagca gggcctaccc   3600 caccccctg aggagcaaga agaccatgct ggtgcagaag aacgtgacca gcgagagcac   3660
ctgctgcgtg gccaagagct acaacaggg gaccgtgatg ggcggcttca aggtggagaa   3720
ccacaccgcc tgccactgca gcacctgcta ctaccacaag agctaatgac catggacact   3780
ccagtgccag caatgacatc tcaggggcca gaggaactgt ccagagagca actctgagat   3840
ctaaggatgt cacagggcca acttgagggc ccagagcagg aagcattcag agagcagctt   3900
taaactcagg gacagagcca tgctgggaag acgcctgagc tcaagccgaa ttccagcaca   3960
ctggcggccg ttactagtgg atccgagctc ggtaccaagc ttatcgatac cgtcgacctc   4020
gaggggccgc ctgcgggctg ccccgctttg cggacgggct gtcccgcgc gaacggaacg   4080 ttggactttc gttaacattg accaagaact gcatggacct aacattcgat ctcattcagt   4140
attaaagggg ggaggggag ggggttacaa actgcaatag agactgtaga ttgcttctgt   4200
agtgggatct ttgtgaagga accttacttc tgtggtgtga cataattgga caaactacct   4260
acagagattt aaagctctaa ggtaaatata aatttttaa gtgtataatg tgttaaacta   4320
ctgattctaa ttgtttgtgt attttagatt ccaacctatg gaactgatga atgggagcag   4380
tggtggaatg cctttaatga ggaaaacctg ttttgctcag aagaaatgcc atctagtgat   4440
gatgaggcta ctgctgactc tcaacattct actcctccaa aaagaagag aaaggtagaa   4500 gaccccaagg acttccttc agaattgcta agttttttga gtcatgctgt gtttagtaat   4560
agaactcttg cttgctttgc tatttacacc acaaaggaaa aagctgcact gctatacaag   4620
aaaattatgg aaaaatattc tgtaaccttt ataagtaggc ataacagtta taatcataac   4680
```

```
atactgtttt ttcttactcc acacaggcat agagtgtctg ctattaataa ctatgctcaa   4740
aaattgtgta cctttagctt tttaatttgt aaaggggtta ataaggaata tttgatgtat   4800
agtgccttga ctagagatca taatcagcca taccacattt gtagaggttt tacttgcttt   4860
aaaaaacctc ccacacctcc ccctgaacct gaaacataaa atgaatgcaa ttgttgttgt   4920
taacttgttt attgcagctt ataatggtta caaataaagc aatagcatca caaatttcac   4980
aaataaagca ttttttcac tgcattctag ttgtggtttg tccaaactca tcaatgtatc   5040
ttatcatgtc tggatcccg ggtaccgagc tcgaattcgt aatcatgtca tagctgtttc   5100
ctgtgtgaaa ttgttatccg ctcacaattc cacacaacat acgagccgga agcataaagt   5160
gtaaagcctg gggtgcctaa tgagtgagct aactcacatt aattgcgttg cgctcactgc   5220
ccgctttcca gtcgggaaac ctgtcgtgcc agctgcatta atgaatcggc caacgcgcgg   5280
ggagaggcgg tttgcgtatt gggcgctctt ccgcttcctc gctcactgac tcgctgcgct   5340
cggtcgttcg gctgcggcga gcggtatcag ctcactcaaa ggcggtaata cggttatcca   5400
cagaatcagg ggataacgca ggaaagaaca tgtgagcaaa aggccagcaa aaggccagga   5460
accgtaaaaa ggccgcgttg ctggcgtttt tccataggct ccgcccccct gacgagcatc   5520
acaaaaatcg acgctcaagt cagaggtggc gaaacccgac aggactataa agataccagg   5580
cgtttccccc tggaagctcc ctcgtgcgct ctcctgttcc gaccctgccg cttaccggat   5640
acctgtccgc ctttctccct tcgggaagcg tggcgctttc tcatagctca cgctgtaggt   5700
atctcagttc ggtgtaggtc gttcgctcca agctgggctg tgtgcacgaa ccccccgttc   5760
agcccgaccg ctgcgcctta tccggtaact atcgtcttga gtccaacccg gtaagacacg   5820
acttatcgcc actggcagca gccactggta acaggattag cagagcgagg tatgtaggcg   5880
gtgctacaga gttcttgaag tggtggccta actacggcta cactagaaga acagtatttg   5940
gtatctgcgc tctgctgaag ccagttacct tcggaaaaag agttggtagc tcttgatccg   6000
gcaaacaaac caccgctggt agcggtggtt tttttgtttg caagcagcag attacgcgca   6060
gaaaaaaagg atctcaagaa gatcctttga tcttttctac ggggtctgac gctcagtgga   6120
acgaaaactc acgttaaggg attttggtca tgagattatc aaaaaggatc ttcacctaga   6180
tccttttaaa ttaaaaatga agttttaaat caatctaaag tatatatgag taaacttggt   6240
ctgacagtta ccaatgctta atcagtgagg cacctatctc agcgatctgt ctatttcgtt   6300
catccatagt tgcctgactc cccgtcgtgt agataactac gatacgggag ggcttaccat   6360
ctggccccag tgctgcaatg ataccgcgag acccacgctc accggctcca gatttatcag   6420
caataaacca gccagccgga agggccgagc gcagaagtgg tcctgcaact ttatccgcct   6480
ccatccagtc tattaattgt tgccgggaag ctagagtaag tagttcgcca gttaatagtt   6540
tgcgcaacgt tgttgccatt gctacaggca tcgtggtgtc acgctcgtcg tttggtatgg   6600
cttcattcag ctccggttcc caacgatcaa ggcgagttac atgatccccc atgttgtgca   6660
aaaaagcggt tagctccttc ggtcctccga tcgttgtcag aagtaagttg gccgcagtgt   6720
tatcactcat ggttatggca gcactgcata attctcttac tgtcatgcca tccgtaagat   6780
gcttttctgt gactggtgag tactcaacca agtcattctg agaatagtgt atgcggcgac   6840
cgagttgctc ttgcccggcg tcaatacggg ataataccgc gccacatagc agaactttaa   6900
aagtgctcat cattggaaaa cgttcttcgg ggcgaaaact ctcaaggatc ttaccgctgt   6960
tgagatccag ttcgatgtaa cccactcgtg cacccaactg atcttcagca tcttttactt   7020
tcaccagcgt ttctgggtga gcaaaaacag gaaggcaaaa tgccgcaaaa aagggaataa   7080
```

```
gggcgacacg gaaatgttga atactcatac tcttcctttt tcaatattat tgaagcattt   7140
atcagggtta ttgtctcatg agcggataca tatttgaatg tatttagaaa aataaacaaa   7200
taggggttcc gcgcacattt ccccgaaaag tgccacctga cgtctaagaa accattatta   7260
tcatgacatt aacctataaa aataggcgta tcacgaggcc ctttcgtctc gcgcgtttcg   7320
gtgatgacgg tgaaaacctc tgacacatgc agctcccgga gacggtcaca gcttgtctgt   7380
aagcggatgc cgggagcaga caagcccgtc agggcgcgtc agcgggtgtt ggcgggtgtc   7440
ggggctggct taactatgcg gcatcagagc agattgtact gagagtgcac catatgcgag   7500
ccaagactgc cactgcactc cagcctggtt cccaatagac cctgaaggcc ctacaggttg   7560
tcttcccaac ctgccccttg ctccatacca cccgcctcca ccccataata ttatacaagg   7620
acacctagtc aaacaaaatg atgcaactta attttattag acaaggctg gtgggcactg   7680 gagtagcacc ttccacgacc aggagaggca ctggggaggg gtcacaggga tgccacccgg   7740
gcagctagaa gccacagctg cagttagtct ttcttctcgt agacttcaaa cttatacttg   7800 atgcctttt cctcctggac ctcagagagg acgcctgggt attctgggag aagtttatat   7860
ttccccaaat caatttctgg gaaaaacgtg tcactttcaa attcctgcat gatccttgtc   7920
acaaagagtc tgaggtggcc tggttgattc atggcttcct ggtaaacaga actgcctccg   7980
actatccaaa ccatgtctac tttacttgcc aattccggtt gttcaataag tcttaaggca   8040
tcatccaaac ttttggcaag aaaatgagct cctcgtggtg gttctttgag ttctctactg   8100
agaactatat taattctgtc ctttaaaggt cgattcttct caggaatgga gaaccaggtt   8160
ttcctaccca taatcaccag attctgttta ccttccactg aagaggttgt ggtcattctt   8220
tggaagtact tgaactcgtt cctgagcgga ggccagggta ggtctccgtt cttgccaatc   8280 cccatattt gggacacggc gacgatgcag ttcaatggtc gaaccatgat ggaagcttgg   8340
aggtgcacac caatgtggtg aatggtcaaa tggcgtttat tgtatcgagc taggcactta   8400
aatacaatat ctctgcaatg cggaattcag tggttcgtcc aatccatgtc agacccgtct   8460
gttgccttcc taataaggca cgatcgtacc accttacttc caccaatcgg catgcacggt   8520 gcttttctc tccttgtaag gcatgttgct aactcatcgt taccatgttg caagactaca   8580
agagtattgc ataagactac atttccccct ccctatgcaa aagcgaaact actatatcct   8640
gaggggactc ctaaccgcgt acaaccgaag ccccgctttt cgcctaaaca caccctagtc   8700
ccctcagata cgcgtatatc tggcccgtac atcgcgaagc agcgcaaaac gcctaaccct   8760
aagcagattc ttcatgcaat tgtcggtcaa gccttgcctt gttgtagctt aaattttgct   8820
cgcgcactac tcagcgacct ccaacacaca agcagggagc agatactggc ttaactatgc   8880
ggcatcagag cagattgtac tgagagtgca ccatatggtg cactctcagt acaatctgct   8940
ctgcagatct ggcctccgcg ccgggttttg gcgcctcccg cgg                     8983
```

<210> SEQ ID NO 8
<211> LENGTH: 26
<212> TYPE: DNA
<213> ORGANISM: Artificial
<220> FEATURE:
<223> OTHER INFORMATION: Asc-CMV-F Primer

<400> SEQUENCE: 8
ggcgcgcctt tgctcacat ggctcg                                          26

<210> SEQ ID NO 9
<211> LENGTH: 33

```
<212> TYPE: DNA
<213> ORGANISM: Artificial
<220> FEATURE:
<223> OTHER INFORMATION: Pac-CMV-R Primer

<400> SEQUENCE: 9
ccttaattaa gagctgtaat tgaactggga gtg                                    33

<210> SEQ ID NO 10
<211> LENGTH: 23
<212> TYPE: DNA
<213> ORGANISM: Artificial
<220> FEATURE:
<223> OTHER INFORMATION: Asc-SV40-F Primer

<400> SEQUENCE: 10
ggcgcgccgc atacgcggat ctg                                               23

<210> SEQ ID NO 11
<211> LENGTH: 34
<212> TYPE: DNA
<213> ORGANISM: Artificial
<220> FEATURE:
<223> OTHER INFORMATION: Pac-SV40-R Primer

<400> SEQUENCE: 11
ccttaattaa gttcgagact gttgtgtcag aaga                                   34

<210> SEQ ID NO 12
<211> LENGTH: 22
<212> TYPE: DNA
<213> ORGANISM: Artificial
<220> FEATURE:
<223> OTHER INFORMATION: beta-NotI-F Primer

<400> SEQUENCE: 12
gcggccgcat acgcggatct gc                                                22

<210> SEQ ID NO 13
<211> LENGTH: 29
<212> TYPE: DNA
<213> ORGANISM: Artificial
<220> FEATURE:
<223> OTHER INFORMATION: beta-NotI-R Primer

<400> SEQUENCE: 13
gcggccgctc actcattagg caccccagg                                         29
```

FSH PRODUCING CELL CLONE

CROSS-REFERENCE TO RELATED APPLICATIONS

The present application is a U.S. National Stage entry under 35 U.S.C. §371 of International Application No. PCT/EP2008/058274, filed Jun. 27, 2008, designating the United States of America and published in English on Dec. 31, 2008, which in turn claims priority to European Patent Application No. 07111257.7, filed Jun. 28, 2007, which is incorporated herein by reference in its entirety.

The present invention relates to nucleic acid molecules comprising a nucleic acid sequence coding for the α- and the β-chain of the human follicle stimulating hormone (FSH), respectively, wherein the nucleic acid sequence has been modified with respect to the codon usage in CHO cells, in comparison to the wild-type human FSH nucleic acid sequence.

The present invention further relates to a recombinant nucleic acid molecule comprising such nucleic acid sequences and host cells containing such recombinant nucleic acid molecules, as well as their use in the production of recombinant human FSH.

Finally, the present invention also relates to a method for producing host cells expressing human follicle stimulating hormone by transfecting cells in suspension culture under serum-free conditions with the recombinant nucleic acid molecule of the present invention.

Follicle stimulating hormone (FSH) is produced by the gonadotrophic cells of the anterior pituitary and released into the circulation. FSH acts together with the luteinizing hormone (LH) in the control of oocyte maturation in females and of spermatogenesis in males. Both FSH and LH belong to a family of heterodimeric glycoproteins which consist of two non-covalently linked α- and β-chains which are encoded by separate genes. While the amino acid sequence of the α-chain of FSH and LH is identical, the amino acid sequence of the β-chain is different in both proteins. Both the α- and the β-chains are glycosylated. The α-chain of FSH has two potential asparagine-linked glycosylation sites at positions 52 and 78, while the β-chain of FSH has two potential asparagine-linked glycosylation sites at positions 7 and 24 (Olijve et al. (1996) Mol. Hum. Reprod. 2(5): 371-382).

Human FSH is used to treat women with unovulation, for stimulation of multifollicular development (superovulation) and in preparation for an assisted conception such as IVF, GIFT or ZIFT. Furthermore, human FSH is used to stimulate the maturation of follicles in women with a low or absent FSH production and for the stimulation of spermatogenesis in men with congenital or acquired hypogonadotropic hypogonadism.

Originally, FSH for medicinal uses was purified from human post-menopausal urine. However, this purified FSH has the disadvantage that it also contains LH and other contaminating proteins of human origin. Furthermore, the use of such a natural source implies limited product availability and consistency.

With the advent of recombinant DNA technology, it became possible to produce human FSH in cell cultures transfected with the nucleic acid sequences coding for the α- and the β-chain. DNA sequences coding for the α- and the β-chains and methods for producing recombinant human FSH have been disclosed e.g. in WO 88/10270, WO 86/04589 and EP 0 735 139.

Currently, there are two commercial recombinant human FSH products on the market in Germany, namely GONAL-F® and PUREGON®, both of which are produced by expression of the wild-type DNA coding for the α- and the β-chains in CHO cells.

However, there is still a need to optimize the expression of the FSH chains to improve the yield and expression rate of FSH for a given number of cells. It is thus a problem underlying the present invention to provide nucleic acid sequences and recombinant nucleic acid molecules by which recombinant human FSH can be produced in large quantities in eukaryotic cells.

According to the present invention, this and further problems are solved by means of the features of the main claim.

Advantageous embodiments are defined in the sub-claims.

According to the present invention, nucleic acid molecules comprising modified nucleic acid sequences coding for the α- and the β-chain of human FSH which have been adapted to the codon usage in chinese hamster ovary (CHO) cells are used for transfecting CHO cells and lead to a significant increase in FSH production in the transfected CHO cells.

In the context of the present invention, the term "increase in FSH production" refers to the situation that upon expressing the modified nucleic acid sequences in the host cell, a higher amount of FSH is produced in a host cell compared to the situation where a non-modified nucleic acid sequence encoding FSH with the same amino acid sequence is expressed in the same type of host cells under similar conditions such as e.g. comparable transfection procedures, comparable expression vectors etc.

The genetic code is redundant, as 20 amino acids are specified by 61 triplet codons. Thus, most of the 20 proteinogenic amino acids are coded by several base triplets (codons). The codons which specify a particular amino acid are not used with the same frequency in a specific organism, however, but there are preferred codons, which are used frequently, and rare codons which are used less frequently. Said differences in codon usage are put down to selective evolutionary pressures, and, in particular, to the efficiency of translation. One reason for the lower translation efficiency of rarely occurring codons could be that the corresponding aminoacyl-tRNA pools are depleted and are therefore no longer available for protein synthesis.

Furthermore, different organisms prefer different codons. Thus, for example, the expression of a recombinant DNA originating from a mammalian cell often proceeds only suboptimally in *E. coli* cells. Therefore, the replacement of rarely used codons by frequently used codons can enhance expression in some cases.

For many organisms, the DNA sequence of a larger number of genes is known and there are tables, from which the frequency of the usage of specific codons in the respective organism can be derived. By using said tables, protein sequences can be relatively exactly back-translated to form a DNA sequence, which contains the codons preferred in the respective organism for the different amino acids of the protein. Tables for codon usage can, inter alia, be found at the following internet addresses:
http://www.kazusa.or.ip/codon/index.html; or
http://www.entelechon.com/index.php?id=tools/index.

There are also programs available for reverse translation of a protein sequence, for example the protein sequence of the α- or the β-chain of human FSH, to form a degenerate DNA sequence, like for instance at http://www.entelechon.com/eng/backtranslation.html.

The term "nucleic acid sequence" for the purposes of the present invention relates to any nucleic acid molecule that codes for polypeptides such as peptides, proteins etc. These nucleic acid molecules may be made of DNA, RNA or analogues thereof. However, nucleic acid molecules being made of DNA are preferred.

The person skilled in the art is clearly aware that modification of the starting nucleotide sequence describes the process of optimization with respect to codon usage.

If, for example, the coding sequence of a foreign wild type enzyme is adjusted to the codon usage of CHO cells, the changes introduced can be easily identified by comparing the modified sequence and the starting sequence (see FIGS. 1a and 1b). Moreover, both sequences will code for the same amino acid sequence. The amino acid sequence of the α-chain of human FSH is depicted in SEQ ID No. 5 and the amino acid sequence of the β-chain of human FSH is depicted in SEQ ID No. 6. These amino acid sequences correspond to the wild-type amino acid sequences of the α- and the β-chain of human FSH as deposited under accession number J 00152 in the EMBL database and under accession number NM_000510 in the NCBI database, respectively.

In the case of the α-chain of human FSH the starting nucleic acid sequence is shown in SEQ ID No. 3 and in the case of the β-chain of human FSH the starting nucleic acid sequence is shown in SEQ ID No. 4.

According to the invention, the nucleic acid sequence coding for the α-chain of human FSH is modified with respect to the codon usage in CHO cells at least at 30 positions, preferably at least at 40 positions, particularly preferably at least at 50 positions, also particularly preferably at least at 60 or 70 positions, and most preferably at least at 75 positions compared to the starting sequence.

Further, according to the invention, the nucleic acid sequence coding for the β-chain of human FSH is modified with respect to the codon usage in CHO cells at least at 25 positions, preferably at least at 30 positions, more preferably at least at 40 positions, particularly preferably at least at 50 positions, also particularly preferably at 60 positions and most preferably at least at 65 positions compared to the starting sequence.

Most preferably, the modified nucleic acid sequence coding for the β-chain of human FSH is the coding region of the nucleic acid sequence given in SEQ ID No. 1 or a nucleic acid sequence which is identical to the coding region of the nucleic acid sequence given in SEQ ID No. 1 by at least 90%, preferably by at least 92% or 94%, particularly preferably by at least 96% or 98%, and most preferably by at least 99% over the entire coding region. In SEQ ID No. 1 the coding region starts at nucleotide 56 and extends up to nucleotide 442.

Most preferably, the optimized nucleic acid sequence coding for the α-chain of human FSH is the coding region of the nucleic acid sequence given in SEQ ID No. 2, or a nucleic acid sequence which is identical to the coding region of the nucleic acid sequence given in SEQ ID No. 2 by at least 85%, preferably by at least 87% or 90%, particularly preferably by at least 92% or 94% and most preferably by at least 96%, 98% or 99% over the entire coding region. In SEQ ID No. 2 the coding region starts at nucleotide 19 and extends up to nucleotide 366.

The terms "non-modified nucleic acid sequence", "wild-type nucleic acid sequence" or "starting nucleic acid sequence" for the purposes of the present invention relate to a nucleic acid sequence which is intended to be used for (over) expression in a host cell and which has not been adapted to the codon usage in the host cell, but is the actual wild-type nucleic acid sequence coding for the protein.

The terms "modified nucleic acid sequence" or "optimized nucleic acid sequence" for the purposes of the present invention relate to a sequence that has been modified for expression in a host cell by adapting the sequence of the non-modified/starting nucleic acid sequence to the codon usage of the host cell. A modified or optimized nucleic acid sequence codes for a protein having the same amino acid sequence as the protein encoded by the non-modified sequence.

Sequence identity is determined by a number of programs based on different algorithms. Herein, the algorithms of Needleman and Wunsch or Smith and Waterman achieve particularly reliable results. For sequence comparisons, the program PileUp (Feng and Doolittle (1987) *J. Mol. Evolution.* 25: 351-360; Higgins et al. (1989) CABIOS 5: 151-153) or the programs Gap and Best Fit (Needleman and Wunsch (1970) *J. Mol. Biol.* 48: 443-453 and Smith and Waterman (1981) *Adv. Appl. Math.* 2: 482-489) were used, which are contained in the GCG software package (Genetics Computer Group, 575 Science Drive, Madison, Wis., USA).

The sequence identity values given herein in percent were determined with the program Gap over the entire sequence region with the following settings: Gap Weight: 50, Length Weight: 3, Average Match: 10,000, and Average Mismatch: 0.000.

Unless specified otherwise, said settings were used as standard settings for sequence comparisons.

Without intending to be bound by a hypothesis, it is assumed that the codon-optimized DNA sequences allow a more efficient translation and the mRNAs formed thereof possibly have a longer half-life period in the cell and are therefore more frequently available for translation.

The person skilled in the art is well familiar with techniques that allow to change the original starting nucleic acid sequence into a modified nucleic acid sequence encoding polypeptides of identical amino acid but with different codon usage. This may e.g. be achieved by polymerase chain reaction based mutagenesis techniques, by commonly known cloning procedures, by chemical synthesis etc.

Also an object of the present invention is a recombinant nucleic acid molecule comprising a modified nucleic acid sequence coding for the β-chain of human FSH wherein the modified nucleic acid sequence is selected from the group consisting of the coding region of the nucleotide sequence according to SEQ ID No. 1 and nucleotide sequences having a sequence identity of at least 90% to the coding region of the nucleotide sequence as depicted in SEQ ID No. 1 and wherein the modified nucleic acid sequence is under the control of a promoter which is active in a host cell.

The term "promoter which is active in a host cell" is intended to mean that the promoter within the recombinant nucleic acid molecule allows the expression of the nucleic acid sequence in a host cell in which the expression of the nucleic acid sequence is desired. The activity of a promoter is usually determined by the presence of transcription factors which are able to bind to the promoter and to activate transcription.

Promoters which are suitable for the expression of nucleic acid sequences in mammalian cells are well known to the person skilled in the art and include viral promoters such as a CMV, SV40, HTLV or adenovirus major late promoter and other promoters such as the EF-1α-promoter or the UbC promoter.

The term "host cell" for the purposes of the present invention refers to any cell that is commonly used for expression, i.e. transcription and translation of nucleic acid sequences for the production of e.g. polypeptides. In particular, the term "host cell" or "organism" relates to prokaryotes, lower eukaryotes, plants, insect cells or mammalian cell culture systems. Preferably, the host cell is a mammalian cell, more preferably the host cell is a rodent cell, even more preferably the host cell is a rodent cell which has a similar codon usage as the CHO cell and most preferably this host cell is a CHO cell.

The host CHO cell line used for expression of the modified sequences and for the production of recombinant human FSH is a derivative of a CHO-K1 cell line and is deficient in dihydrofolate reductase (dhfr) activity. The cell line was obtained from DSMZ (Cat. No. ACC 126) and adapted to suspension and serum-free culture conditions.

A CHO cell line containing a recombinant nucleic acid molecule comprising a first optimized nucleic acid sequence coding for the β-chain of human FSH and a second optimized nucleic acid sequence coding for the α-chain of human FSH was deposited on 28 Mar. 2007 at the DSMZ in Braunschweig under deposit number DSM ACC2833.

The term "recombinant nucleic acid molecule" within the meaning of the present invention is intended to comprise all kinds of nucleic acid molecules which are capable of being introduced into a host cell and effecting the expression of a nucleic acid sequence which is contained within the recombinant nucleic acid molecule. The term comprises, inter alia, plasmid vectors and viral vectors such as adenoviral, lentiviral and retroviral vectors, with plasmid vectors being preferred.

Examples of suitable plasmid vectors which can be used to express proteins in mammalian cells are well known and include for example the pCI vector series, pSI (Promega), pcDNA® vectors, pCEP4, pREP4, pSHOOTER™, pZeoSV2 (Invitrogen), pBlast, pMono, pSELECT, pVITRO and pVIVO (InVivogen). Besides the promoter and the nucleic acid sequence to be expressed, a recombinant nucleic acid molecule usually contains other functional elements such as polyadenylation sequences, prokaryotic and/or eukaryotic selection genes which allow the identification of positively transformed prokaryotic and/or eukaryotic cells, and an origin of replication. The expert knows which elements he has to select for a specific purpose and which plasmid vector is suitable for the expression of a specific nucleic acid sequence in a specific host cell.

Recombinant nucleic acid molecules comprising the nucleic acid sequences of the present invention can be obtained by standard molecular biological methods which are described in the literature, e.g. in Sambrook and Russell (2001) Molecular cloning—a laboratory manual, 3$^{rd}$ edition, Cold Spring Harbour Laboratory Press, Cold Spring Harbour, N.Y., USA.

Preferably, the recombinant nucleic acid molecule of the present invention comprises both a modified nucleic acid sequence coding for the β-chain of human FSH and a nucleic acid sequence coding for the α-chain of FSH.

The nucleic acid sequence coding for the α-chain of human FSH is selected from an optimized nucleic acid sequence coding for the α-chain of human FSH which is selected from the group consisting of the coding region of the nucleic acid sequence according to SEQ ID No. 2, nucleic acid sequences having a sequence identity of at least 85% to the coding region of the nucleic acid sequence as depicted in SEQ ID No. 2, the coding region of the non-modified nucleic acid sequence as depicted in SEQ ID No. 3 and nucleic acid sequences having a sequence identity of at least 70% to the coding region of the nucleic acid sequence as depicted in SEQ ID No. 3.

The nucleic acid sequence coding for the α-chain of human FSH may be under the control of the same promoter as the nucleic acid sequence coding for the β-chain of human FSH, for example by means of an internal ribosome entry site (IRES), or it may be under the control of a separate promoter. Preferably, the nucleic acid sequence coding for the α-chain of human FSH is under the control of a separate promoter. More preferably, the nucleic acid sequence coding for the optimized β-chain of human FSH is under the control of an SV40 promoter and the nucleic acid sequence coding for the α-chain of human FSH is under the control of a CMV promoter. Most preferably, the recombinant nucleic acid molecule of the present invention has the nucleic acid sequence depicted in SEQ ID No. 7.

The present invention further relates to a host cell which contains a recombinant nucleic acid molecule comprising the optimized nucleic acid sequence coding for the β-chain of human FSH and which further contains a nucleic acid sequence coding for the α-chain of human FSH which is selected from a modified nucleic acid sequence selected from the group consisting of the coding region of the nucleotide sequence according to SEQ ID No. 2 and nucleotide sequences having a sequence identity of at least 85% to the coding region of the nucleic acid sequence as depicted in SEQ ID NO. 2 and the coding region of the non-modified nucleic acid sequence as depicted in SEQ ID No. 3 and nucleic acid sequences having a sequence identity of at least 70% to the coding region of the nucleic acid sequence as depicted in SEQ ID No. 3.

The nucleic acid sequence coding for the α-chain of human FSH may be present in the same recombinant nucleic acid molecule as the optimized nucleic acid sequence coding for the β-chain of human FSH, or it may be introduced into the host cell on a separate recombinant nucleic acid molecule. Preferably, the nucleic acid sequence coding for the α-chain of human FSH is present in the same recombinant nucleic acid molecule as the optimized nucleic acid sequence coding for the β-chain of human FSH.

The host cell may be selected from mammalian cell culture systems such as NIH3T3 cells, CHO cells, COS cells, 293 cells, Jurkat cells, BHK cells and HeLa cells. Preferably, the host cell is a rodent cell, more preferably the host cell is a rodent cell which has a similar codon usage as the CHO cell and most preferably this host cell is a CHO cell.

Also an object of the present invention is a cell culture comprising the host cells containing a recombinant nucleic acid molecule comprising a modified nucleic acid sequence coding for the β-chain of human FSH and a nucleic acid sequence coding for the α-chain of human FSH, wherein the nucleic acid sequence coding for the α-chain may be selected from the group consisting of the non-modified nucleic acid sequence and the modified nucleic acid sequence as defined above, in a suitable culture medium.

The cell culture is obtained by cultivating the host cells in a suitable culture medium under conditions which support the growth of the host cells.

The term "cultivating cells" is to be understood to mean that the cells are kept in vivo under conditions that allow proliferation, normal metabolism of the cells and formation of the recombinant protein. That means that the cells are provided with all necessary nutrients as well as with oxygen and are kept at a suitable pH and a suitable osmolarity. The cells may be cultivated in any suitable manner. Preferably, the cells are cultivated as suspension culture, for example in flasks or in roller flasks. The term "cultivation" includes batch cultivation, fed-batch cultivation as well as perfusion cultures and other suitable culture methods.

"Cultivating in suspension" means that the cells do not adhere to a surface, but are distributed in the culture medium.

"Batch cultivation" within the meaning of the present invention is a cultivation method in which culture medium is neither added nor withdrawn during the cultivation.

A "fed-batch method" within the meaning of the present invention is a cultivation method in which culture medium is added during the cultivation, but no culture medium is withdrawn.

"Perfusion culturing" within the scope of the present invention is a cultivation method in which culturing medium is withdrawn and new culture medium is added during cultivation.

The culture medium preferably has only a low serum content, e.g. a maximum content of 1% (v/v) serum; most preferably, the medium is serum-free. Examples of suitable culture media are basal media such as RPMI 1640, DMEM, F12, ProCHO5 or eRDF, which may be mixed with each other and with supplements according to the need of the cells. In addition to glucose and amino acids, the medium may contain chelators such as aurin tricarboxylic acid (ATA), anorganic salts such as phosphate salts, polyamines and their precursors such as putrescine, hormones such as insulin, antioxidants such as ascorbic acid and vitamin mixtures, lipid precursors such as ethanolamine and cell-protecting substances such as pluronic F68. The expert knows which culture medium to use for the cultivation of the specific cell type. Preferably, the culture medium is ProCHO5.

Also an object of the present invention is a method in which a host cell according to the present invention is first cultured in a suitable culture medium for a certain period of time and then the cell culture supernatant is harvested.

The "cell culture supernatant" is the cell culture medium which was in contact with the cells for a certain period of time and which has then been separated from the cells. The cell culture supernatant contains the recombinant protein produced by the cells. The cells may be separated from the supernatant by conventional separation techniques such as filtration and centrifugation. In long-term cultures, the supernatant of the host cells according to the present invention contains FSH concentrations of at least 500 ng/ml, preferably et least 1000 ng/ml, more preferably at least 1500 ng/ml and most preferably at least 2000 ng/ml.

The recombinant human FSH may be purified from the cell culture supernatant by one or more purification steps. Suitable purification methods are known to the expert and include ion exchange chromatography, hydrophobic interaction chromatography, hydroxyapatite chromatography, affinity chromatography and gel filtration. Methods for purifying recombinant human FSH are disclosed e.g. in WO 00/63248, WO 2006/051070 and WO 2005/063811.

For administration as a medicament, the purified recombinant human FSH is mixed with one or more excipients to obtain a formulation which can be administered to patients. Suitable formulations for recombinant human FSH are disclosed inter alia in EP 0 853 945, EP 1 285 665, EP 0 974 359, EP 1 188 444 and EP 1 169 349.

The host cell of the present invention is produced by transfecting cells with a recombinant nucleic acid molecule of the present invention which comprises either only the modified nucleic acid sequence coding for the β-chain of human FSH or also a nucleic acid sequence coding for the α-chain of human FSH. Alternatively, the nucleic acid sequence coding for the β-chain and the nucleotide sequence coding for the α-chain may be present on separate recombinant nucleic acid molecules which are introduced into the host cell either simultaneously or successively.

Suitable transfection methods are known to the person skilled in the art and include for example calcium phosphate precipitation, DEAE-dextran-mediated transfection, electroporation and lipofection. Commercially available kits for transfection, such as SuperFect, PolyFect, Effectene (Qiagen), TransFast™, ProFection®, Transfectam® (Promega) and TransPass™ (NEB) may also be used. Preferably, the cells are transfected while in suspension and are transfected under serum-free conditions.

For the production of recombinant human FSH on a commercial scale, the cells are usually stably transfected, which means that successfully transformed cells are selected after transfection by means of a selection agent which kills the non-transfected cells, whereas the transfected cells containing the resistance gene continue growing. Suitable selection reagents include antibiotics such as zeocin, neomycin and puromycin and other drugs such as methotrexate.

The present invention is illustrated by means of the following examples, which are not to be understood as limiting.

EXAMPLES

1. Cloning of a Recombinant Nucleic Acid Molecule Comprising Optimized Nucleic Acid Sequences Coding for the α- and the β-Chain of Human FSH A pUC18 vector backbone was used which already contained an SV40 polyadenylation site and splice site and a dhfr gene cassette consisting of an RSV promoter, the mouse dihydrofolate reductase gene and an SV40 polyadenylation and splice site. The dihydrofolate reductase gene enables the selection of positively transfected cells and the amplification of the transfected gene with the drug methotrexate.

The non-modified sequences of the α- and the β-chain of human FSH were derived from Fiddes and Goodman (1979) Nature 281: 351-356 and Jameson et al. (1988) Mol. Endocrinol. 2(9): 806-815, respectively. These sequences were optimized in that the coding regions were adapted to the codon usage in frequently used CHO genes.

Furthermore, an additional stop codon was introduced to ensure efficient termination of translation. The optimized nucleotide sequences for the β- and the α-chain are depicted in SEQ ID No. 1 and 2, respectively, and a comparison of the wild-type and the modified nucleic acid sequences is shown in FIGS. 1a and 1b. The sequence comparison shows that the modified and the non-modified nucleic acid sequence coding for the α-chain of human FSH are 80% identical, whereas the modified and the non-modified nucleic acid sequence coding for the β-chain of human FSH are 85% identical.

The modified sequences were inserted separately into two copies of the pUC18 backbone by cutting them with the restriction enzymes SacII and NcoI and subsequent ligation.

The CMV promoter and the SV40 promoter were amplified from suitable template DNA with the following primers, simultaneously introducing an AscI and a PacI restriction site (underlined in the following primers):

```
Asc-CMV-F Primer
                                        (SEQ ID No. 8)
5'-GGC GCG CCT TTT GCT CAC ATG GCT CG-3'

Pac-CMV-R Primer
                                        (SEQ ID No. 9)
5'-CCT TAA TTA AGA GCT GTA ATT GAA CTG GGA GTG-3'

Asc-SV40-F Primer
                                        (SEQ ID No. 10)
5'-GGC GCG CCG CAT ACG CGG ATC TG-3'

Pac-SV40-R Primer
                                        (SEQ ID No. 11)
5'-CCT TAA TTA AGT TCG AGA CTG TTG TGT CAG AAG
A-3'
```

The CMV promoter was introduced into the plasmid containing the α-chain of human FSH by cutting the plasmid with the restriction enzymes AscI and PacI and ligation and the SV40 promoter was introduced into the plasmid containing the β-chain of human FSH by cutting the plasmid with the restriction enzymes AscI and PacI and ligation.

Finally, the expression cassette for the β-chain of human FSH comprising the SV40 promoter, the nucleic acid sequence coding for the β-chain and the SV40 polyadenylation signal was amplified with the following primers, simultaneously introducing a NotI restriction site both on the 5' and on the 3' end of the amplificate (underlined in the following primers):

```
beta-NotI-F Primer
                                      (SEQ ID No. 12)
5'-GCG GCC GCA TAC GCG GAT CTG C-3' beta-NotI-R Primer
                                      (SEQ ID No. 13)
5'-GCG GCC GCT CAC TCA TTA GGC ACC CCA GG-3'
```

The amplificate was then inserted into the NotI-cut plasmid containing the α-chain of human FSH. The resulting plasmid containing both the optimized nucleic acid sequence coding for the α-chain and the optimized nucleic acid sequence coding for the β-chain is shown in FIG. 2. The sequence of the plasmid with both optimized nucleic acid sequences is depicted in SEQ ID No. 7.

2. Transient Transfection of CHO Cells with Recombinant Nucleic Acid Molecules Containing Different Combinations of α- and β-Chains of Human FSH Plasmids containing either an optimized nucleic acid sequence coding for the α-chain or an optimized nucleic acid sequence coding for the β-chain in combination with the corresponding wild-type β-chain or α-chain or containing both optimized sequences, were produced as described under 1) above. The DNA was mixed with the medium ProCHO5 (Lonza) containing 8 mM glutamine without HT to a total volume of 200 μl. Then 20 μl of the SuperFect reagent (Qiagen) was added to the DNA solution and mixed. This mixture was then incubated for 5-10 minutes at room temperature.

Aliquots containing 1.68×10⁶ CHO cells were centrifuged (5 min, 800 rpm, 18-25° C.), the supernatant was removed and the cells were resuspended in 1.1 ml culture medium ProCHO5 containing 8 mM glutamine without HT. The suspension was then transferred to the DNA mixture, after the DNA mixture had been incubated for 5-10 minutes, mixed and transferred to a well of a 6-well plate. The cells were incubated for 3 hours at 37° C., which incubation leads to the adherence of the cells. The supernatant was removed, the cells were washed three times with 1 ml PBS and then fresh culture medium (2 ml ProCHO5 containing 8 mM glutamine without HT) was added. After 2 days incubation at 37° C., the supernatant was removed and centrifuged. The supernatant was concentrated (concentration factor 16.67) and the FSH concentration was determined in an ELISA reader (Anogen). The results of this measurement are shown in FIG. 3.

The results show that the introduction of a modified α-chain in combination with a wild-type β-chain leads to a reduction of expression of almost 50% as compared to a combination of two wild-type chains. In contrast, the introduction of a modified β-chain, both in combination with a wild-type and the modified α-chain, leads to a transient FSH expression which is enhanced by a factor of 1.5-3 as compared to the combination of the wild-type α-chain and the wild-type β-chain. Therefore, in particular the use of the modified β-chain leads to a significant enhancement of FSH expression after transient transfection, whereas the modified α-chain does not positively influence FSH production.

BRIEF DESCRIPTION OF THE DRAWINGS

FIG. 1: Comparison of the non-modified and the modified nucleic acid sequences coding for the α-chain and the β-chain of human FSH a) Sequence comparison of the modified and the non-modified nucleic acid sequence coding for the α-chain of human FSH pXM17ss#6: part of a plasmid containing the modified nucleic acid sequence coding for the α-chain of human FSH (SEQ ID No. 2)

wt α FSH: non-modified nucleic acid sequence coding for the α-chain of human FSH (SEQ ID No. 3)

The start codon and the stop codons are shown in bold letters.

b) Sequence comparison of the modified and the non-modified nucleic acid sequence coding for the β-chain of human FSH Query: non-modified nucleic acid sequence coding for the β-chain of human FSH (SEQ ID No. 4)

Subject: modified nucleic acid sequence coding for the β-chain of human FSH (SEQ ID No. 1)

The start and the stop codons are shown in bold letters.

Figure 2:
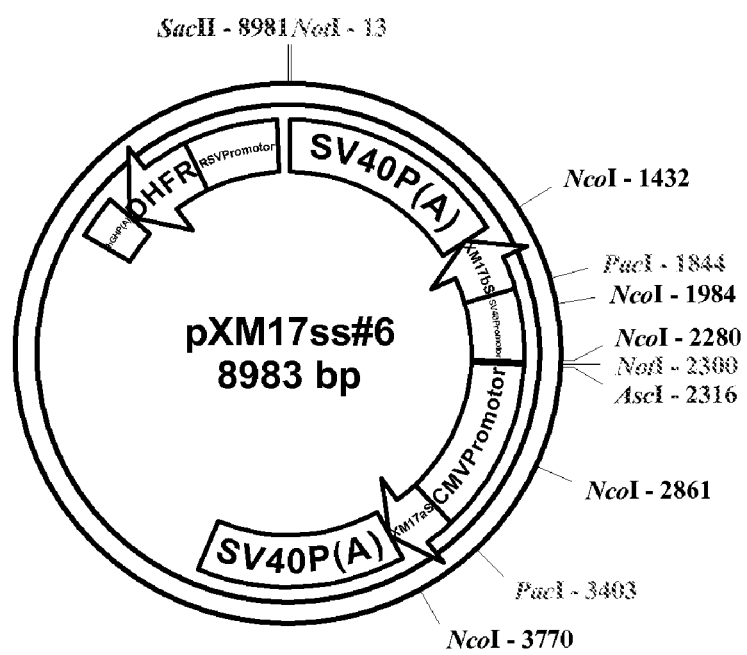
Figure 3:
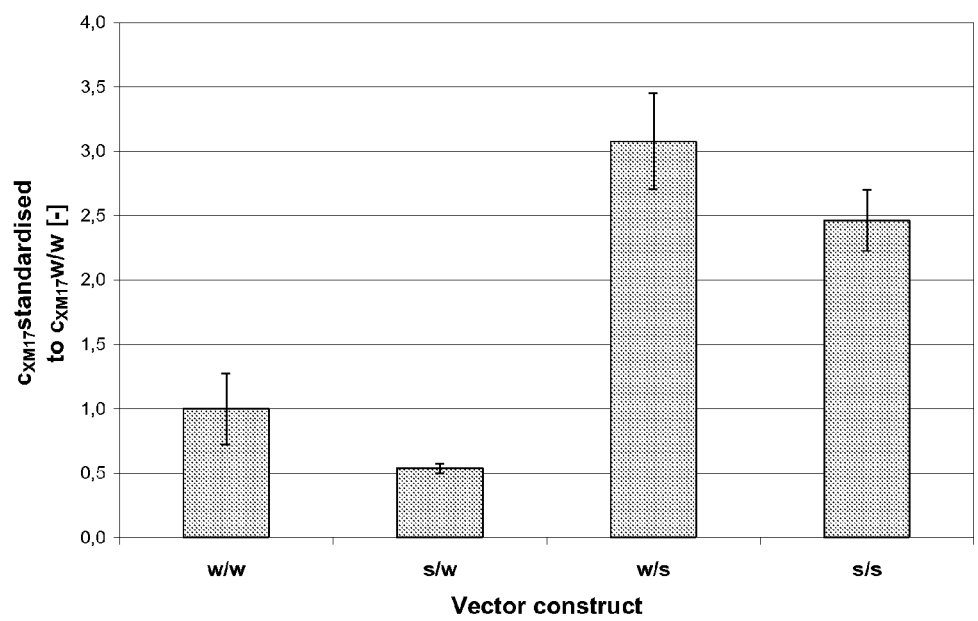

FIG. 2: Map of the recombinant nucleic acid molecule containing both the modified nucleic acid sequence coding for the α-chain of human FSH and the modified nucleic acid sequence coding for the β-chain of human FSH FIG. 3: Expression analysis of different combinations of α- and β-chains after transient expression in CHO cells The relative FSH expression in relation to cells expressing a combination of the wildtype α- and β-chains is shown.

w/w: non-modified α- and β-chain
s/w: modified α-chain and non-modified β-chain
w/s: modified β-chain and non-modified α-chain
s/s: modified α- and β-chain

The invention claimed is:

1. A nucleic acid molecule comprising a nucleic acid sequence coding for the β chain of human follicle stimulating hormone (FSH), which is selected from the group consisting of the coding region of the nucleic acid sequence according to SEQ ID NO: 1 and nucleic acid sequences having a sequence identity of at least 98% to the coding region of the nucleic acid sequence as depicted in SEQ ID NO: 1.

2. A nucleic acid molecule comprising a nucleic acid sequence coding for the α chain of human follicle stimulating hormone (FSH), which is selected from the group consisting of the coding region of the nucleic acid sequence according to SEQ ID NO: 2 and nucleic acid sequences having a sequence identity of at least 98% to the coding region of nucleic acid sequence as depicted in SEQ ID NO: 2.

3. A recombinant nucleic acid molecule comprising a first nucleic acid sequence according to claim 1 under the control of a promoter which is active in a host cell.

4. The recombinant nucleic acid molecule according to claim 3, further comprising a second nucleic acid sequence according to claim 2.

5. The recombinant nucleic acid molecule according to claim 3, further comprising a second nucleic acid sequence which is selected from the group consisting of the coding region of the nucleic acid sequence according to SEQ ID NO: 3 and nucleic acid sequences having a sequence identity of at least 70% to the coding region of the nucleic acid sequence as depicted in SEQ ID NO: 3.

6. The recombinant nucleic acid molecule according to claim 4, wherein the second nucleic acid sequence is under the control of a separate promoter.

7. The recombinant nucleic acid molecule according to claim 3, wherein the first nucleic acid sequence is under the control of a viral promoter.

8. The recombinant nucleic acid molecule according to claim 7, wherein the first nucleic acid sequence is under the control of an SV40 promoter.

9. The recombinant nucleic acid molecule according to claim 7, wherein the second nucleic acid sequence is under the control of a CMV promoter.

10. The recombinant nucleic acid molecule according to claim 3, having the nucleic acid sequence as depicted in SEQ ID NO: 7.

11. A host cell containing a recombinant nucleic acid molecule according to claim 4.

12. The host cell according to claim 11, wherein the host cell is a mammalian cell.

13. The host cell according to claim 11, wherein the host cell is a Chinese hamster ovary (CHO) cell.

14. The host cell according to claim 11, wherein the host cell corresponds to that having the deposit number DSM ACC2833.

15. A host cell containing a first recombinant nucleic acid molecule according to claim 3 and a second recombinant nucleic acid molecule comprising a nucleic acid sequence selected from the nucleic acid sequence according to claim 2 and the nucleic acid sequence as depicted in SEQ ID NO: 3.

16. A cell culture comprising the host cell of claim 11 in a suitable culture medium.

17. A method for producing recombinant human FSH, comprising the steps of:
culturing the host cell of claim 11 in a suitable culture medium; and
harvesting the cell culture supernatant.

18. The method according to claim 17, further comprising the step of purifying the recombinant human FSH from the cell culture supernatant.

19. A method for producing the host cell according to claim 11, comprising transfecting cells in suspension culture under serum-free conditions with the recombinant nucleic acid molecule according to claim 4.

20. A method for producing the host cell according claim 15, comprising transfecting cells in suspension culture under serum-free conditions with a first recombinant nucleic acid molecule according to claim 3 and a second recombinant nucleic acid molecule comprising a nucleic acid sequence selected from the nucleic acid sequence according to claim 2 and the nucleic acid sequence as depicted in SEQ ID NO: 3.

21. A method for producing recombinant human FSH, comprising the steps of:
culturing the host cell of claim 15 in a suitable culture medium; and
harvesting the cell culture supernatant.

22. The method according to claim 21, further comprising the step of purifying the recombinant human FSH from the cell culture supernatant.

* * * * *